United States Patent [19]

Moreth et al.

[11] Patent Number: 4,723,436
[45] Date of Patent: Feb. 9, 1988

[54] PROCESS FOR CALIBRATING A GAS METERING INSTRUMENT

[75] Inventors: Benno Moreth, Lubeck; Kurt Leichnitz, Gross Grönau, both of Fed. Rep. of Germany

[73] Assignee: Dragerwerk Aktiengesellschaft, Fed. Rep. of Germany

[21] Appl. No.: 873,194

[22] Filed: Jun. 11, 1986

[30] Foreign Application Priority Data

Jun. 15, 1985 [DE] Fed. Rep. of Germany ....... 3521535

[51] Int. Cl.$^4$ ............................................. G01N 1/22
[52] U.S. Cl. ...................................................... 73/1 G
[58] Field of Search ......................................... 73/1 G

[56] References Cited

U.S. PATENT DOCUMENTS

| 3,618,363 | 11/1971 | Kraus ................... | 73/1 G |
| 3,948,604 | 4/1976 | Hoppesch ................ | 73/1 G |

FOREIGN PATENT DOCUMENTS

| 2804288 | 8/1979 | Fed. Rep. of Germany ....... | 73/1 G |
| 3213241 | 10/1983 | Fed. Rep. of Germany ....... | 73/1 G |
| 0128840 | 8/1982 | Japan ................................. | 73/1 G |
| 0160056 | 10/1982 | Japan ................................. | 73/1 G |

Primary Examiner—Michael J. Tokar
Assistant Examiner—Robert R. Raevis
Attorney, Agent, or Firm—McGlew and Tuttle

[57] ABSTRACT

A process for calibrating a gas metering instrument comprises flushing a test chamber with a flushing gas and subsequently filling it with a calibrating gas having a predetermined composition of carrier substance and carrier gas. The calibrating gas does not have to be carried and made available constantly in its predetermined composition. Thereby a reduction in the volume of the gas metering instrument is obtained. For this purpose, provisions are made so that a feed device introduces a specified amount of calibrating substance from a reservoir into the heat chamber, whereupon the calibrating substance mixes with the flushing gas in the test chamber to form the calibrating gas of predetermined composition. In addition, equipment is described for implementing the process of calibrating a gas metering instrument.

1 Claim, 1 Drawing Figure

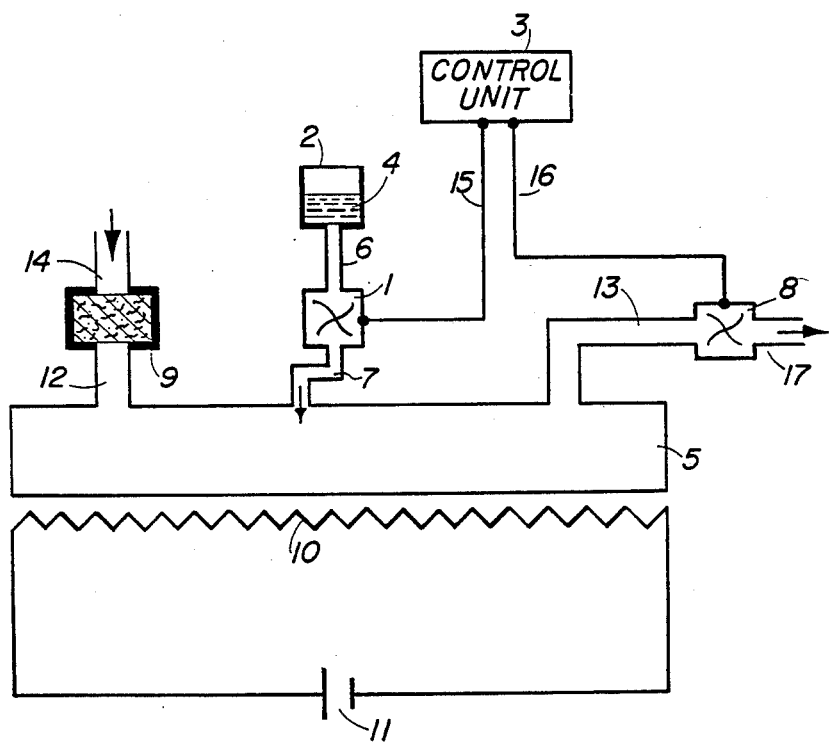

PROCESS FOR CALIBRATING A GAS METERING INSTRUMENT

FIELD AND BACKGROUND OF THE INVENTION

The invention relates to a process of calibrating a gas metering instrument, in which a test chamber, before the introduction of the gas to be tested, is flushed with a flushing gas and subsequently filled with a calibrating gas having a predetermined composition of calibrating substance and carrier gas. Moreover, suitable equipment for implementing the process is described.

During the long term use of gas metering equipment which determines the gas composition in a test chamber, it is always necessary to carry out a calibration of the measuring arrangement as a whole at certain intervals of time. For this purpose, a test gas of fixed composition is conducted from a storage tank into the test chamber. However, before this can be done, it is necessary to flush the test chamber with a flushing gas, generally air, in order to flush out residual amounts of test gas, which may still be present, and to prevent distortion of the calibration value. To carry out the calibration, expensive pipelines and switching arrangements are required in order to supply metered amounts of (a) test gas, (b) flushing gas (inert gas) and (c) calibrating gas at the correct times. In addition, storage facilities for the premixed calibrating gas must be provided.

Such a process and equipment for implementing it is described in U.S. Pat. No. 3,792,272.

During the test cycle, a test chamber is filled over a test pipeline with the gas to be tested and the gas is analyzed in this test chamber. When a calibration of the test chamber is necessary, a flushing pipeline is connected, over suitable switching elements, to the test chamber. Through said flushing pipeline, ambient air is introduced as flushing gas into the test chamber. After the test chamber has been flushed, an additional calibrating gas pipeline is connected in a further step to the test chamber and the test chamber is disconnected from the pipeline carrying the flushing air, so that a calibrating gas of a particular composition flows through the calibrating gas pipeline into the test chmber. After the calibration is concluded, the calibrating gas pipeline is closed and the test chamber is connected to the test gas pipeline.

In the known process, it is a disadvantage that the calibrating gas tank thaaht has to be provided must contain a supply of premixed calibrating gas in large volume. For a calibration, not only the test chamber itself, but also the gas pipelines must be flushed. This increases the consumption of calibrating gas and a corresponding amount must be made available. The preparation of the calibration gas of predetermined composition is expensive and it must moreover be made available in a careful manner. For example, care must be taken to ensure that, while the gas metering instrument is being used, the composition of the calibrating gas does not change. For example, a component of the calibrating gas may condense or otherwise be deposited in the pipelines and may not reach the test chamber. Consequently, stabilizers must be added to the calibrating gas under certain conditions or care must be taken to ensure that the tanks containing the calibrating gas are exchanged from time to time.

SUMMARY OF THE INVENTION

It is therefore an object of the invention under discussion to improve the process of calibrating a gas metering instrument in such a manner, that the calibrating gas does not have to be carried and made available constantly in its predetermined composition and that a reduction in the volume of the gas metering instrument is achieved therewith.

This objective is accomplished due to the fact that a feed device of the invention introduces an amount of calibrating substance, specified by a control unit, from a reservoir into the test chamber, whereupon the calibrating substance is mixed with the flushing gas in the test chamber to form a calibrating gas of predetermined composition.

The advantage of the invention is to be seen in that the calibrating gas is produced in the test chamber itself only when needed, as a result of which it becomes possible to store the calibrating substance in the form in which it is most stable, requires less space and can be transported advantageously. The calibration with the calibrating gas can be carried out simply without additional expenditure for pipelines and with the least consumption of calibrating substance.

Equipment for implementing the process comprises a feed device, which is connected over a feed pipeline to a reservoir containing the calibrating substance and over a delivery pipeline to the test chamber. Such equipment brings the amount of calibrating substance required for the calibrating gas directly into the test chamber, in which it mixes with the flushing gas present there to form a calibrating gas of predetermined composition.

The calibrating substance in the reservoir may comprise a stable, highly concentrated gas or, advantageously, also a liquid, which is introduced into the test chamber, in which it is vaporized. In the case of liquids of high vapor pressure, the vapor phase may also be introduced into the test chamber by the feed device.

For metering uniform and reproducible amounts of calibrating substance, a metering pump is advantageously used.

The time at which a calibrating substance is metered and the duration of the metering process are fixed by a control unit.

Accordingly an object of the present invention is to provide a process for calibrating a gas metering instrument having a test chamber, comprising passing a flushing gas through the metering chamber to flush the metering chamber before a gas is to be tested, introducing a selected amount of calibrating substance into the test chamber and mixing to form a mixture of flushing gas and calibrating substance in the test chamber which is used to calibrate the gas metering instrument before a gas is tested.

A further object of the present invention is to provide an apparatus for performing this process.

A still further object of this invention is to provide an apparatus for calibrating a gas metering instrument which is simple in design, rugged in construction and economical to manufacure.

An example of the operation of equipment for implementing the process to calibrate gas metering equipment is shown schematically by means of the single figure and explained in greater detail in the following.

BRIEF DESCRIPTION OF THE DRAWING

The only figure of the drawing is a block diagram schematically showing the apparatus of the present invention.

DESCRIPTION OF THE PREFERRED EMBODIMENT

The block flow diagram of the equipment shows a test chamber 5, which has a gas inlet duct 12 and a gas outlet duct 13. In addition, it is connected to a delivery pipeline 7, over which the calibrating substance 4 is introduced by means of a feed device constructed as a metering pump 1 from the reservoir 2 through the feed pipeline 6 into the test chamber 5. A feed pump 8 with an outflow pipeline 17 is connected to the gas outlet duct 13. Metering pump 1 and feed pump 8 are connected to a control unit 3 over appropriate control leads 15 and 16. For producing stable temperature conditions, the test chamber 5 is provided with a heater 10, which is supplied with energy from a voltage source 11.

To carry out the calibration process, the feed pump 8 is first of all operated over the contol unit 3 and the control lead 16, as a result of which the interior of the test chamber 5 is flushed with the amount of flushing air, flowing in through the connection tube 14, the filter 9 and the gas inlet duct 12. After a specifiable period of time, the feed pump 8 is switched off and the metering pump 1 is switched on by control unit 3 over control lead 15. Thereupon, a known amount of calibrating substance 4, determined by the length of time that the metering pump is switched on, which in turn is fixed by the control unit 3, is transported from the reservoir 2 through the feed pipeline 6 and the delivery pipeline 7 into the test chamber. There it is mixed with the flushing gas in the test chamber 5 to forma calibrating gas of predetermined composition, which is fixed by the ratio of the flushing gas to the calibrating substance. The mixing of calibrating substance 4 and flushing gas is fostered by the convection produced within the test chamber 5 by the heater 10, i.e. gas rises and circulates due to the heat at the bottom of chamber 5.

As noted above, the flushing substance may simply be filtered air. The calibration substance may be any appropriate substance for the equipment. For example, if the content of chlorine in a sample is to be tested by the equipment, the calibration substance can be liquid chlorine.

While a specific embodiment of the invention has been shown and described in detail to illustrate the application of the principles of the invention, it will be understood that the invention may be embodied otherwise without departing from such principles.

What is claimed is:

1. A device for providing a calibrating gas to a test chamber comprising a reservoir containing a liquid calibrating substance, a metering pump for feeding emtered amounts of the liquid calibrating substance, a feed pipeline connected between the reservoir and the metering pump for conveying liquid calibrating substance from the resrvoir to the metering pump, a delivery pipeline connected between the metering pump and the chamber for supplying metered amounts of the liquid calibrating substance to the chamber, flushing gas supplying means connected to the chamber for supplying flushing gas at predetermined rates through the chamber, a flushing gas inlet duct connected to the chamber for receiving flushing gas into the chamber, a gas outlet duct connected to the chamber for discharging gas from the chamber, a feed pump connected in the gas outlet duct for drawing gas out of the chamber while flushing gas is being drawn into the chamber through the gas inlet duct, and control means connected to said feed pump and to said metering pump for controlling said metering pump and said feed pump at predetermiend selected rates to form a mixture of calibrating substance and flushing gas in the chamber.

* * * * *